US007936913B2

United States Patent
Nordell et al.

(10) Patent No.: US 7,936,913 B2
(45) Date of Patent: May 3, 2011

(54) NETWORK IMAGE REVIEW IN CLINICAL HEMATOLOGY

(75) Inventors: Peter W. Nordell, Beverly, MA (US); Albert A. Eliasen, Eden Prairie, MN (US)

(73) Assignee: NextSlide Imaging LLC, Gates Mills, OH (US)

( * ) Notice: Subject to any disclaimer, the term of this patent is extended or adjusted under 35 U.S.C. 154(b) by 938 days.

(21) Appl. No.: 11/834,996

(22) Filed: Aug. 7, 2007

(65) Prior Publication Data

US 2009/0041329 A1    Feb. 12, 2009

(51) Int. Cl.
G06K 9/00    (2006.01)

(52) U.S. Cl. .................................... 382/134; 382/128

(58) Field of Classification Search .................. 382/133, 382/134

See application file for complete search history.

(56) References Cited

U.S. PATENT DOCUMENTS

| | | | | |
|---|---|---|---|---|
| 6,169,816 | B1 * | 1/2001 | Ravkin | 382/128 |
| 6,198,839 | B1 | 3/2001 | Kuan et al. | 382/133 |
| 6,226,392 | B1 * | 5/2001 | Bacus et al. | 382/128 |
| 6,633,662 | B2 * | 10/2003 | Ravkin | 382/133 |
| 7,187,790 | B2 * | 3/2007 | Sabol et al. | 382/128 |
| 7,359,536 | B2 * | 4/2008 | Hays et al. | 382/128 |
| 2002/0068856 | A1 | 6/2002 | Gelfand et al. | 600/300 |
| 2003/0231791 | A1 | 12/2003 | Torre-Bueno et al. | 382/133 |
| 2006/0050948 | A1 * | 3/2006 | Sumida et al. | 382/133 |
| 2006/0109343 | A1 * | 5/2006 | Watanabe et al. | 348/79 |
| 2006/0274946 | A1 * | 12/2006 | Karlsson | 382/199 |
| 2006/0291712 | A1 * | 12/2006 | Popescu et al. | 382/134 |
| 2007/0014460 | A1 * | 1/2007 | Kuziela et al. | 382/128 |

FOREIGN PATENT DOCUMENTS

EP    1 308 712 A2    5/2003

OTHER PUBLICATIONS

International Search Report and Written Opinion for PCT/US2008/009324, mailed Mar. 25, 2009.

* cited by examiner

*Primary Examiner* — David P Rashid
(74) *Attorney, Agent, or Firm* — Gilman Clark LLC; T. J. Clark

(57) ABSTRACT

Embodiments of the invention provide techniques for using digital imaging and networked communications in clinical hematology. An Area of Interest (AOI) on a slide is determined. A high resolution image of the AOI is analyzed for sample integrity and adjusted and rescanned based on programmable parameters. Sensitive HIPAA information is removed from the AOI image stored on a server. The server includes Web 2.0 software applications. A remote user reviews the image and adds metadata to the server. The server manages the work flow between the stored AOI images and the available users. A technician accesses information about a particular image file, as well as other topics, through knowledge management and social network applications. Lab reports are generated based on the metadata. The quality of the metadata is subject to quality control processes. The stored images and associated metadata can be mined for subsequent medical research.

17 Claims, 8 Drawing Sheets

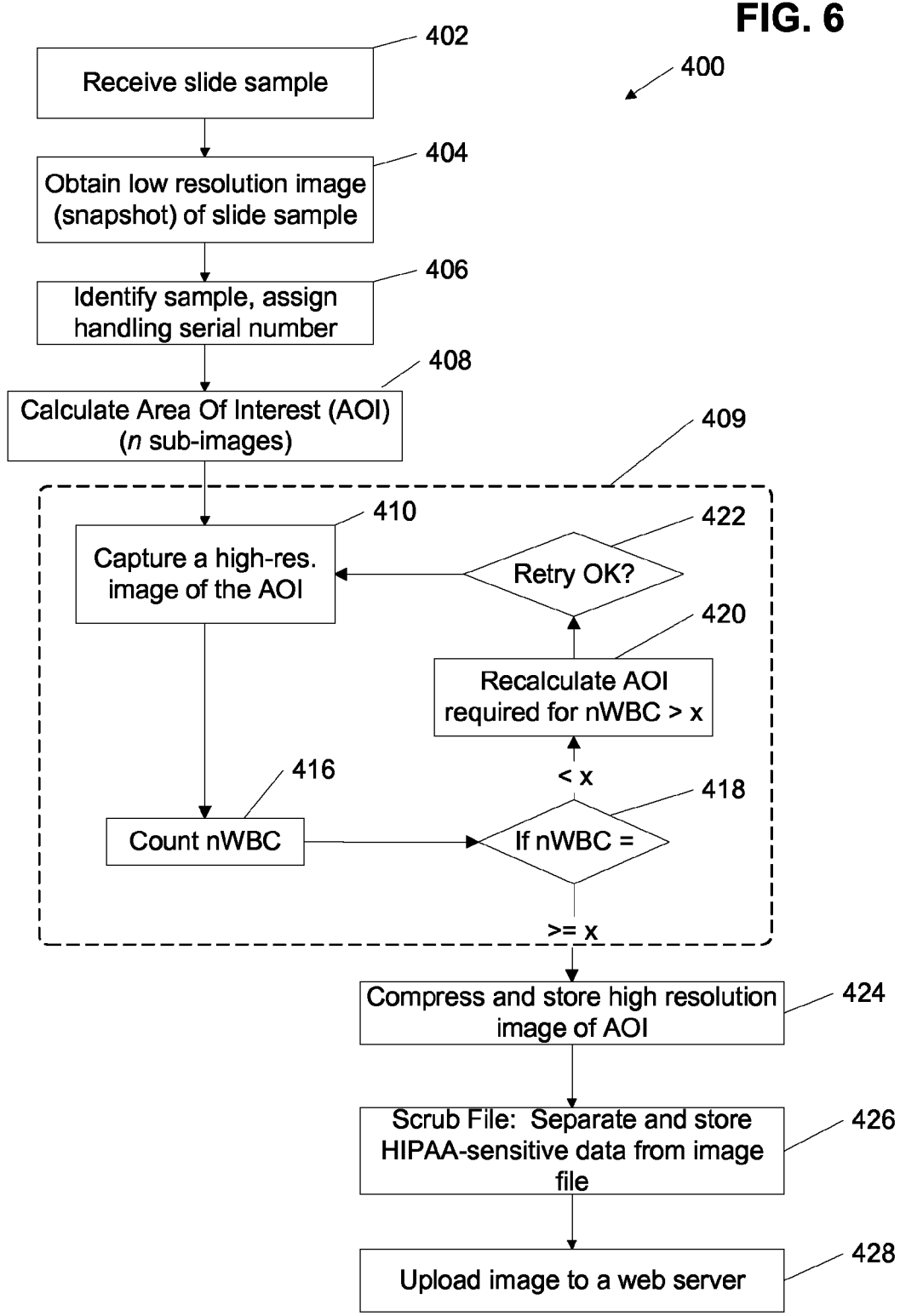

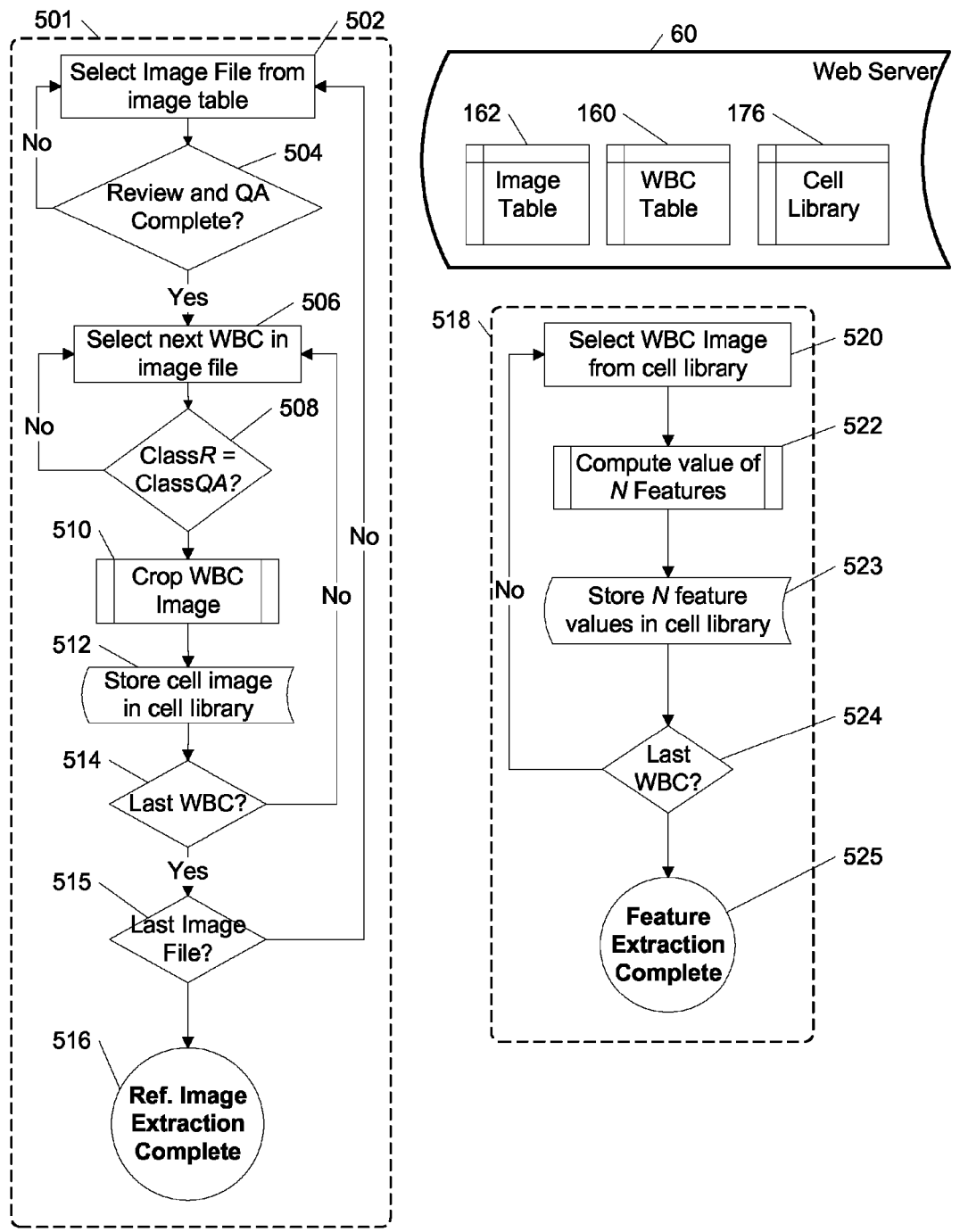

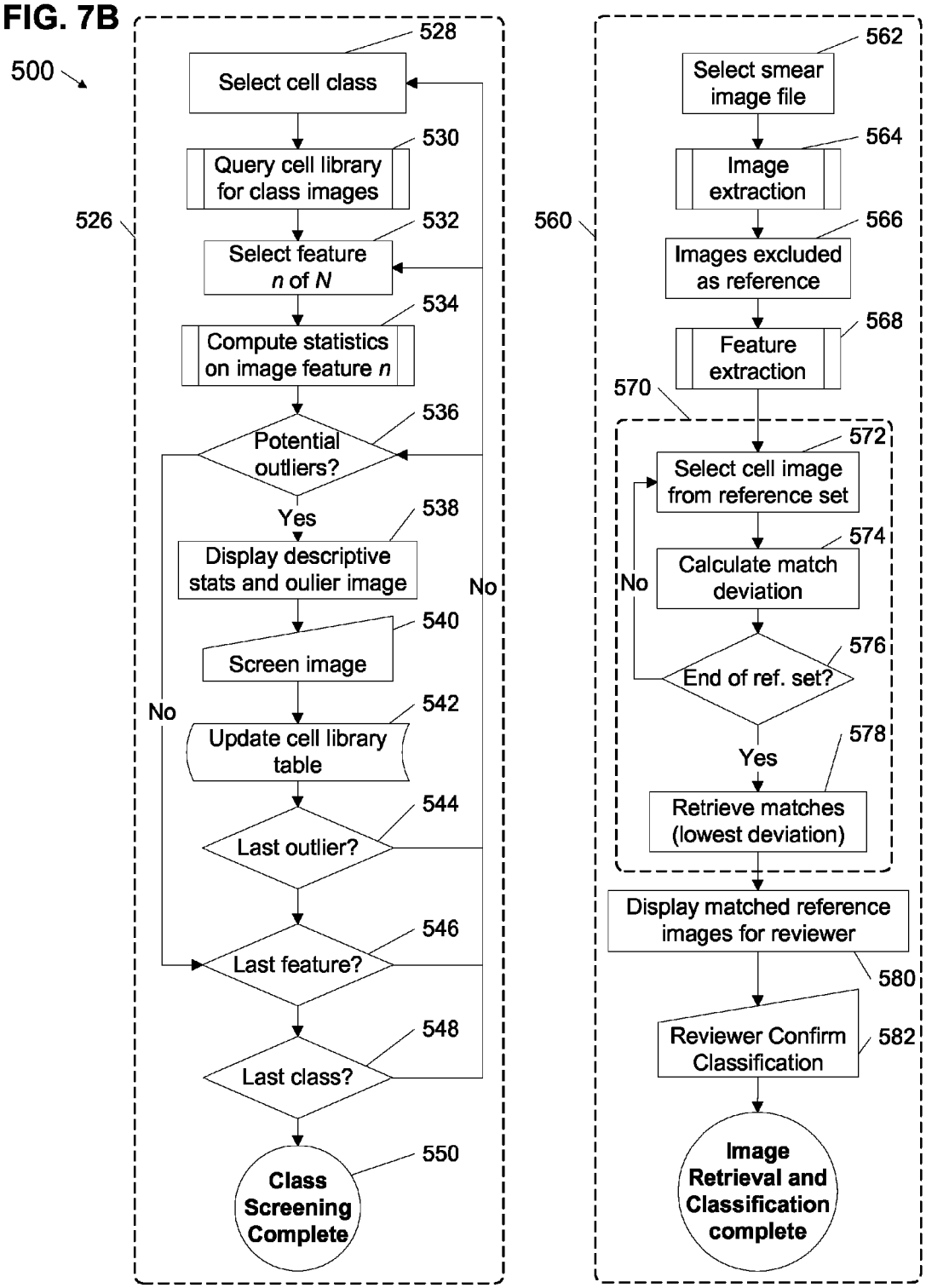

NETWORK IMAGE REVIEW IN CLINICAL HEMATOLOGY

TECHNICAL FIELD

The present invention relates to methods and means of using digital imaging and network communications in clinical hematology.

BACKGROUND

In the healthcare industry, the routine complete blood count (CBC) is a common test. Typically, a blood sample is run through an automated blood analyzer configured to count a large number of red cells (erythrocytes, RBC's), white cells (leukocytes, WBC's), and platelets (thrombocytes). In general, the automated blood analyzer provides an accurate volumetric count of each, along with varying amounts of information regarding the morphology of the counted cells. Based on the analysis, some samples are chosen for manual examination. For example, the manual differential blood count examination (i.e., "manual diff") includes smearing, drying, and staining the blood onto a glass slide. This slide prep is often performed by automated equipment, but is also performed manually, especially in smaller labs. The slide is then examined by a technician or physician (the reviewer) under a microscope using up to 100× magnification oil immersion optics. The examination typically requires the reviewer to count and classify 100 WBC's, examine the shape and color and measure the diameter of RBC's, and make an estimate of the platelet and WBC count per unit area, for example. The data from such a manual examination is usually presented to the clinician with data obtained from an automated blood analyzer and is known as a CBC result, or "CBC with manual diff".

Due to the speed and efficiency of automated blood analyzers, a large portion of the cost of all CBC's is incurred in the labor cost of that subset of samples examined manually. For example, a group of technicians can process between 40 and 70 samples in one eight hour shift. For various reasons (e.g., required training, ergonomic issues and nature of the work), however, in many markets it is difficult to hire skilled technicians. Accordingly, hospital and lab human resource managers generally find it difficult to adequately support the staffing required for extended hours of operation (e.g., $2^{nd}$ and $3^{rd}$ shifts).

Some microscope manufacturers have introduced automated systems for creating a digital image of a slide-mounted sample at some magnification. In general, these tools cover a range of research and clinical applications in medicine, and are configured with different optical, slide handling, camera, and image processing sub-systems depending upon the application. However, the subset of prior art systems that can deliver the optical requirements for hematology generally do not meet the minimum requirements for automation and throughput required in a modern clinical laboratory.

SUMMARY

In accordance with implementations of the invention, one or more of the following capabilities may be provided. Controlling an automated digital microscope to capture an image of a blood smear in a manner effective for high-volume clinical hematology. Automatically selecting at least one of a plurality of available reviewers based upon programmable preferences, including reviewers employed by a lab, network partners, and third-party service providers; electronically transferring image information via a computer network to the selected reviewers. Blood smear image information and associated data can be obtained with manual and assisted modes and then stored, transmitted and processed. Reports on the image of a blood smear can be created, and the quality of a technician's analysis can be monitored. Blood smear image dissemination and data collection can be incorporated into a web based production management system. Image information and data can be archived and mined for use in hematology and other medical research.

In general, in an aspect, the invention provides a hematology review network including a slide imager including a low magnification optical path and a high magnification optical path, and configured to receive a blood smear slide, obtain a low magnification image of at least a portion of the slide, and obtain at least one high magnification image of a portion of the blood smear, an image server operably coupled to the slide imager and configured to compute an area of interest within the low magnification image, direct the slide imager to obtain one or more high magnification images of the entire area of interest, identify white blood cells in the one or more high magnification images, and recompute and rescan a larger area of interest if the count of white blood cells identified in the image is below a threshold value, a web server including a workflow management application, the web server configured to store and disseminate the at least one high magnification image to at least one reviewer, the specific reviewer selected by the workflow management application based on programmable parameters, and at least one review station configured to communicate with the web server, display the at least one high magnification image, and receive an image information input from the specific reviewer, wherein the image information input is stored on the web server.

Implementations of the invention may include one or more of the following features. The high magnification optical path of the slide imager includes a 100× oil immersion objective lens, or a selectable objective head assembly. The slide imager can be a line scan system. The web server includes a knowledge management application configured to provide information relating to blood smear images to the reviewers. The web server includes at least one social networking application configured to allow the reviewers to interact. The review station is configured to sequentially highlight in the displayed high magnification image the identified WBCs, such that the review station displays the feature at higher magnification for detailed examination and classification. The review station is further configured to record the position of and highlight in the display a feature within the high magnification image previously identified by the reviewer, such that the review station displays the feature at higher magnification for detailed examination and classification. The workflow management application is configured to select at least one stored high magnification image and the associated image information input by a first reviewer, wherein the image information is verified by second reviewer. The image information input from the specific reviewer is a cell classification. The hematology review network assembles a reference dataset of cell images used by image processing software applications configured to perform automated image retrieval and cell classification. That output is compared to the input from a specific reviewer. The web server and image server are configured to aggregate high magnification images of blood smears and related metadata across multiple patient populations, and provide the aggregated image and metadata to a data mining application such that HIPAA-sensitive information is not disclosed.

In general, in another aspect, the invention provides a method for obtaining and storing a high magnification image of a blood smear sample including storing a low magnification image of the blood smear sample, determining an area of interest within the blood smear sample based on image analysis of the low magnification image, obtaining at least one high magnification image of at least a portion of the area of interest, counting a number of white blood cell in the at least one high magnification image, adjusting the area of interest within the blood smear sample if the number of white blood cells counted is below a first threshold, creating an image file which includes the at least one high magnification image and excludes HIPAA-sensitive data, and uploading the high magnification image of the area of interest to a web server.

Implementations of the invention may include one or more of the following features. Receiving a blood smear slide including the blood smear sample and a sample identification information, recognizing the sample identification information, and storing the sample identification information. Linking the sample identification information with the image file with an index, such that the sample identification information and the image file persist in different storage locations. The area of interest within the blood smear sample is adjusted if the number of white blood cells imaged is below a preset threshold value. Creating an image file includes assembling high magnification images to create an assembled high magnification image of the area of interest.

In general, in another aspect, the invention provides a hematology services outsourcing application embodied on a computer-readable medium for enabling a distributed computer system, including a web server code segment for residence on a server computer coupled to a plurality of networks to enable the web server to receive, store and disseminate a plurality of blood smear image files, a client computer code segment including a user interface to enable a user of a computer connected to at least one of the networks, to view a blood smear image and enter a white blood cell count corresponding to the number of white blood cells in the blood smear image, such that the white blood cell count is stored on the web server, a scheduling code segment which executes on the web server and controls access to the blood smear image files by the user based on a plurality of workflow parameters, a quality assurance code segment which executes on the web server and enables a quality technician to review information stored on the web server and enter a quality score, such that the quality score is stored on the web server, and a billing code segment which executes on the web server and enables a collection of information on the number of blood smear images viewed by the user, and a computation of costs associated with the user.

Implementations of the invention may include one or more of the following features The client computer code segment enables the user to enter the location and description of at least one nucleated red blood cell, and to store the entered information of the at least one nucleated red blood cell on the web server. The client computer code segment enables the user to measure and enter the measurements and a description of the RBC morphology, and the entered information is stored on the web server. An auction code segment which executes on the web server and enables the user of the client computer code segment to enter a price for their services, such that the web server is configured to disseminate the blood smear image based on the price.

These and other capabilities of the invention, along with the invention itself, will be more fully understood after a review of the following figures, detailed description, and claims.

BRIEF DESCRIPTION OF THE FIGURES

FIG. 6 is process flowchart for hematology image processing.
FIGS. 7A and 7B are a workflow diagram of automated image retrieval and classification.

DETAILED DESCRIPTION OF PREFERRED EMBODIMENTS

Embodiments of the invention provide techniques for using digital imaging and networked communications in clinical hematology. Medical slides containing blood smear samples are loaded into a slide scanning system. A low resolution image of the slide is captured and stored. Relevant slide information (e.g., bar code data, patient information) is stored. An Area of Interest (AOI) on the slide is determined. A high resolution image of the AOI is captured and stored. The high resolution image is analyzed for sample integrity (e.g., white blood cell count, sample area, sample dimensions). The AOI can be adjusted and rescanned based on programmable parameters. The high resolution AOI image and the slide information are separated via an index such that the high resolution AOI image can be stored without the corresponding patient information (e.g., sensitive HIPAA information is removed from the AOI image). The AOI image is compressed and stored on a web server. The web server accessible via a wide area network (e.g., the Internet). The web server includes Web 2.0 software applications (e.g., workflow management, knowledge management, and social networking). A remote user (e.g., technician) can review the image and add metadata to the image information (e.g., white blood cell counts are added to a data field). The web server manages the work flow between the stored AOI images and the available users (i.e., technicians and other reviewers). A technician can access additional information about a particular image file, as well as other topics, through the knowledge management and social network applications. Lab reports are generated based on the metadata provided by the reviewers. The quality of the metadata entered by the reviewers is subject to quality control processes. The stored images and associated metadata can be mined for subsequent medical research. This system is exemplary, however, and not limiting of the invention as other implementations in accordance with the disclosure are possible.

Figure 1:
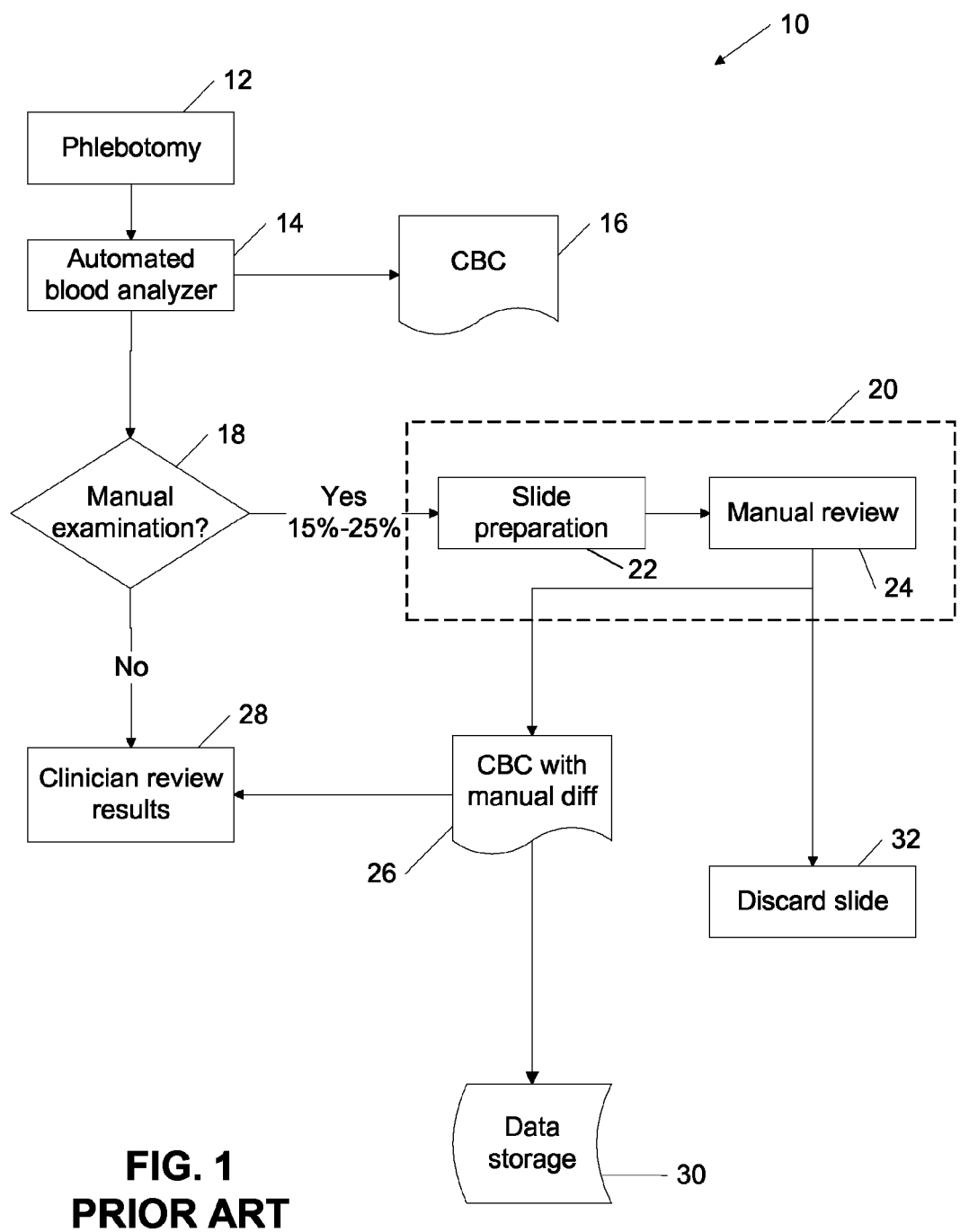
FIG. 1 is a workflow diagram of a prior art hematology lab.

Referring to FIG. 1, a prior art process used in a hematology clinic is shown. The process 10 includes a phlebotomy procedure 12, automated blood analysis 14, a CBC report 16, a decision for manual examination 18, a diff bench 20, slide preparation 22, manual review 24, a CBC with manual diff report 26, clinician review 28, data storage 30, and slide disposal 32. Blood is removed from a patient in a phlebotomy procedure 10 and is generally run through an automated blood analyzer 14. In general, the blood analyzer provides a volumetric count of red blood cells (RBC's), white blood cells (WBC's) and platelets in a sample. The results of the analysis 14 are presented in a Complete Blood Count (CBC) report 16. At stage 18, some blood samples (e.g., 15-25%) are selected for manual examination 24. The manual review 24 requires that blood be smeared onto a glass slide, dried, and stained. In general, the slide preparation 22 is performed by automated equipment, but it is also performed manually, especially in smaller labs. The slide preparation 22 and manual review 24 are usually completed in a laboratory work center commonly called a "diff bench" 20. During the manual review 24, the slide is examined by a technician or physician (i.e., the reviewer) under a microscope using up to 100× magnification oil immersion optics. The data from the manual examination is presented with the data from the automated blood analyzer to the clinician 28 as a CBC result, or "CBC with manual diff" 26. The results 26 may also be stored in an electronic format on a data storage unit 30. In general, it is typical for hematology labs to retain blood slides for two weeks or less. Apart from the data taken by the automated analyzer 14 and the subsequent manual review 24, the entire sample is destroyed 32. Accordingly, the smear can be re-examined only during the retention period.

In general, due to the speed and efficiency of automated blood analyzers, a large portion of the cost of all CBC's is incurred in the labor cost of the subset of samples examined manually on the diff bench 20. Typically, technicians on the diff bench 20 can process between 40 and 70 samples in one eight hour shift, and hourly wages on the diff bench range from $25 to $45 per hour. For example, due to the ergonomics and nature of the work, the labor market for skilled technicians can be tight in some markets; hospital and lab human resource managers can find it difficult to staff the diff bench 20 adequately. For these reasons, the diff bench 20 can be a constraint on operations in clinical hematology labs.

Figure 2:
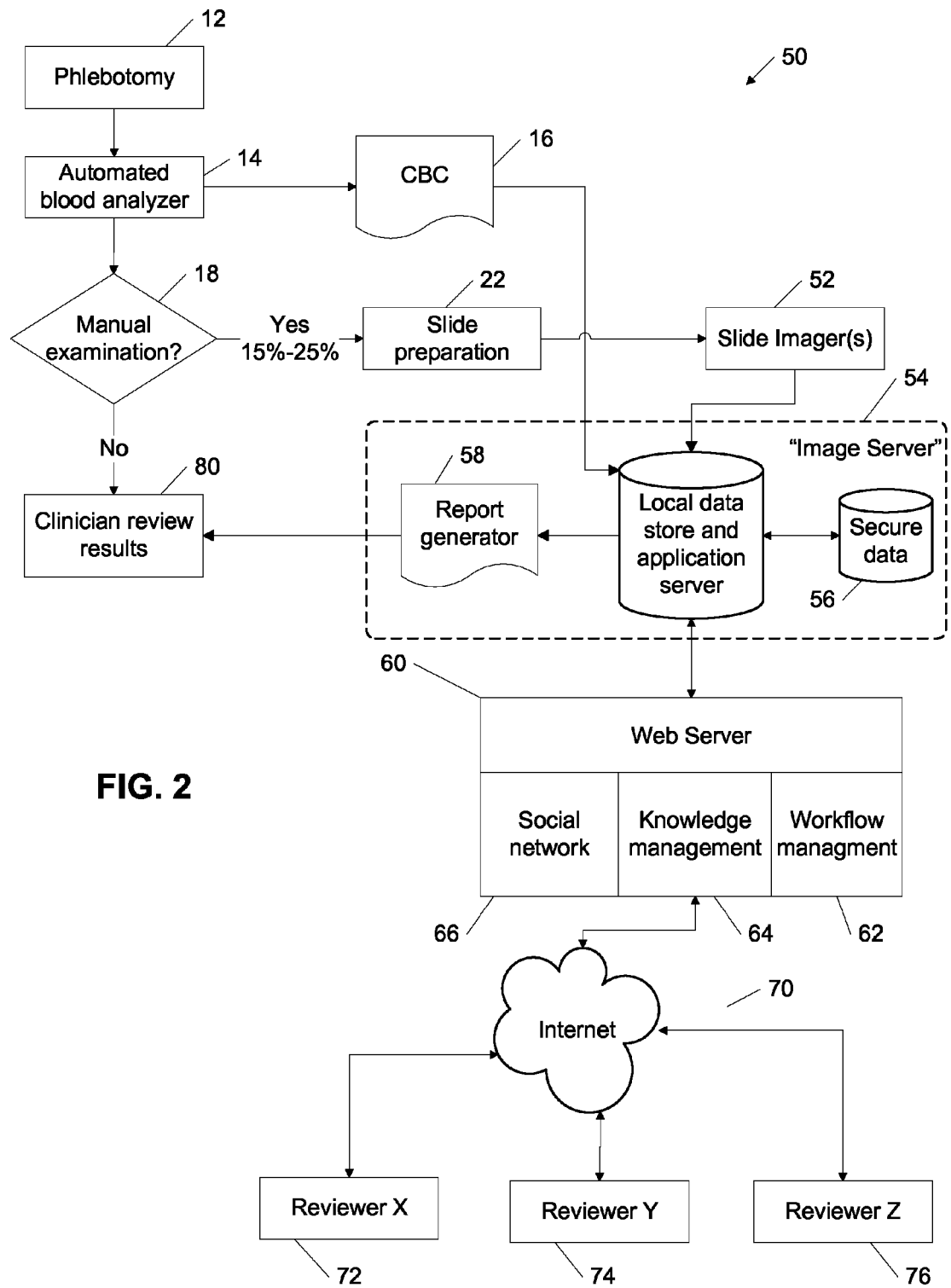
FIG. 2 is a workflow diagram of a hematology review network.

Referring to FIG. 2, with further reference to FIG. 1, a workflow diagram for a hematology network 50 is shown. The hematology network 50 includes a phlebotomy procedure 12, automated blood analyzer 14, CBC report 16, the decision to perform a manual examination 18, slide preparation 22, at least one slide imager 52, local data store and application server (i.e., image server) 54, secure data storage 56, report generator 58, web server 60, workflow management 62, knowledge management 64, social network 66, the Internet 70, reviewers X, Y, and Z 72, 74, 76, and clinician review 80. In general, the phlebotomy 12, analysis 14, CBC report 16, decision for manual examination 18, and slide preparation 22 are as established in the prior art. In general, the slide imager 52 includes image capture and scanning technologies (e.g., slide scanner, CCD, RGB Video camera) configured to provide digital microscopy for clinical hematology.

A consideration in designing any imaging system for clinical hematology labs is slide throughput. As an example, and not a limitation, the requirement of 100× magnification translates to pixel size on the order of 0.10 micron, or 10-7 meter per pixel. A blood smear created during slide preparation 22 may typically cover a 25 mm×25 mm area on the glass slide. Imaging the entire smear would create a raw image file >100 GB of data. At a typical image capture rate of 10 sec/mm 2 @100×, such a system could image ~4 slides on one eight hour shift, impractically slow. A reviewer, however, will typically examine 10 fields of view 50× magnification, each approximately 400 microns, or 0.4 mm in diameter, while performing a manual diff. Since less than 2 mm² of the sample is typically examined, it is unnecessary to create a digital image of the entire smear as long as the image is taken from an appropriate area of each sample. As will be discussed, the slide imager or slide scanner 52 is configured to capture slide information and a low magnification image of the blood smear to determine an appropriate Area of Interest (AOI). The low resolution image is obtained with an auxiliary camera incorporated into the imager 52, or with a lower magnification set of optics. The AOI can be selected based on a set of programmable parameters. For example, the AOI will be a region with a specified cell density with little or no cell overlap, generally termed the monolayer in the prior art. The slide scanner 52 is also configured to capture a high magnification image of the AOI (e.g., with a 100× oil immersion objective). In an embodiment, the slide imager 52 includes a plurality of networked slide imagers configured with different magnification powers such that the coordinates of the AOI on a slide can be transferred from one slide imager 52 to another. For example, a low magnification slide imager is configured to obtain a low magnification image and then transfer the slide and AOI coordinates to a high magnification slide imager.

The at least one slide imager 52 is operably connected to the local data store and application server (i.e., image server) 54. The image server 54 includes processing, storage and input/output devices for receiving, storing, processing and sending blood smear slide information on a network. For example, the application server 54 is a programmable computer running Microsoft Windows® Operating software, and the network includes wired and wireless embodiments. The processing and storage components of the application server 54 includes different physical configurations such that the storage can be a plurality of disk drives, or other persistent memory devices, which are operably connected to the processor. The secure data 56 includes at least a portion of the local data store 54 dedicated to HIPAA sensitive patient data. In one embodiment, the secure data 56 is a dedicated file server protected by security features (e.g., strong passwords, encryption, restricted user groups). The application server 54 is configured to analyze and separate confidential information from slide image files (e.g., image files created by the slide imager 52) to maintain patient confidentiality.

The report generator 58 is a software application configured to output reports based on data contained within each local data store and application server 54. In general, the format and contents of the output of the report generator application 58 is configured according to the requirements of each laboratory site, as well as according to system defaults. For example, the report generator application 58 is configured to output report files in XML and HL7 formats that can be read by most modern laboratory information (i.e., LIS) systems. The report generator application 58 is further configured to output reports in HTML format delivered to users via several methods, including, but not limited to; posting the report to a reviewer website on the web server 60, creating the report on demand from the reviewer website on the web server 60, and sending the report via email (update status or provide a time based report) to a specified user or group of users. The content of the reports generated by the report generator application 58 include, but are not limited to; clinical test results and reports, laboratory operational metrics and records, network component performance such as slide scanner uptime and average throughput, financial data such as billing information, and quality assurance data such as reviewer evaluations and quality audit results.

The image server 54 is operably connected to web sever 60. The web server 60 includes, or is otherwise connected to, software applications for workflow and production management 62, knowledge management 64, and social networking 66 (e.g., Web 2.0). Both the image server 54 and the web server 60 are configured to receive and execute program instructions from a computer-readable medium such as floppy disks, conventional hard disks, CD-ROMS, Flash ROMS, nonvolatile ROM, and RAM. A computer-readable medium also includes program instructions, or other information, received via a communication port transfer (i.e., network downloads). The web server 60 is connected to the internet 70 and is configured to send and receive data from a plurality of users (e.g., reviewers X, Y, Z 72, 74, 76). For example, the reviewers 72, 74, 76 are users of personal computers, where each computer is executing instructions contained on a computer-readable medium, and can receive data via a thin or rich client arrangement (i.e., via a web browser or via a local application with connectivity to the internet). In an embodiment, the reviewers 72, 74, 76 review the image of an AOI and input metadata associated with the image (e.g., WBC count, RBC morphology, other comments). The metadata is then transferred via the web server 60 to the local data store 54. The reviewer 72, 74, 76 may also search topics related to blood smear classifications via the knowledge management 64 (e.g., expert systems, knowledge bases) and social network 66 applications (e.g., chat, messaging, email, file sharing, blogging, and discussion groups).

Figure 3:
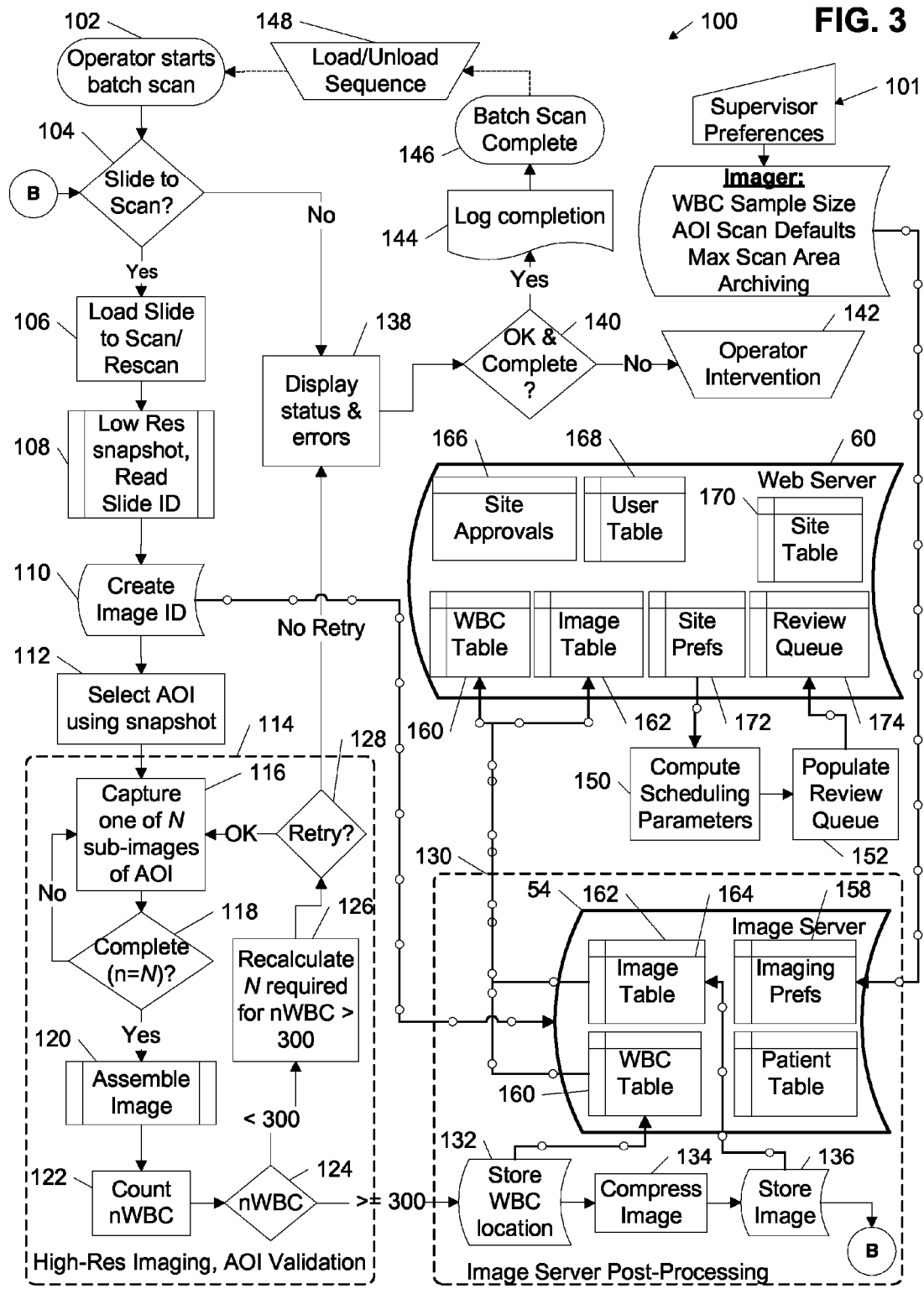
FIG. 3 is a process diagram of a scanner and image server operation.

In operation, referring to FIG. 3, with further reference to FIG. 2, a process 100 for obtaining and storing an image of a blood sample using the network 50 includes the stages shown. The process 100, however, is exemplary only and not limiting. The process 100 may be altered, e.g., by having stages added, removed, or rearranged.

In general, the image server 54 includes a relational database with a plurality of correlated tables, wherein each table includes data fields consisting of various data types. As an example, and not a limitation, the server 54 includes an indexed table of images 162, wherein each image is identified by a unique index variable (i.e., Image ID). The information on the image table 162 includes an image index field, an image file (e.g., .jpg) and image metadata (e.g., AOI dimensions, tile number). The WBC table 160 includes the WBC position and count for each image file. The patient data associated with a particular blood smear Image ID is stored on the image server 54 in a patient table 164. For example, the fields of the patient table 164 include a patient name, social security number, slide ID number and an image index number. The image files stored on the image table 162 are relationally linked to the information in the patient table 164 such that HIPAA sensitive information is stored on the patient table 164, and not within the image table 162. Accordingly, the patient table 164 is stored in a secure data store 56 on the image server 54.

At stage 101, the customer preferences for the blood sample imaging process 100 are stored on the image server in the imaging preferences table 158. For example, a lab supervisor stores parameters for default AOI dimensions, WBC sample limits, and data/file archive details (e.g., location, schedule).

At stage 102, a blood smear sample slide, or batch of blood sample slides (i.e., single slide or batch processing), are received from a slide preparation system 22, or similar operation (e.g., manual slide preparation), and loaded into the slide imager 52. In general, the blood smear on a particular slide covers an approximate area of 25 mm by 25 mm, and each slide includes an identification mark (e.g., ID characters, optical bar code, magnetic strip). In an embodiment, the slides are received by a plurality of networked slide imagers 52.

At stage 104, the process determines whether a slide is available to scan. For example, the batch could be complete, or a slide handling error has occurred. At stage 106, a slide is loaded into the imager 52. For example, the image 52 includes a slide stage configured to position the slide sample under various optical paths, such as a low magnification and high magnification pathways. In this example, each optical path may include an image capture device, such as a CCD camera.

At stage 108, the scanner 52 obtains at least one low resolution image of the blood smear sample. In general, each slide includes identification information (i.e., Slide ID), and the imager 52 is configured to recognize and store the Slide ID. The slide can include a text based alphanumeric ID, and the imager 52 is configured to perform Optical Character Recognition. In an embodiment, the imager 52 includes a bar code scanner to read a bar code on a particular slide. The low resolution image obtained on the imager 52 may include a plurality of low resolution images which are concatenated, or otherwise combined, along each axis to create a variable area low resolution image. For example, the area and dimensions of the low resolution image are program parameters based on a user's requirements (e.g., variations in blood smear sizes, throughput requirements, camera resolution capabilities).

At stage 110, an image identification number (i.e., Image ID) is assigned to the Slide ID and stored in the Image Table on the image server 54.

At stage 112, an Area of Interest (AOI) is computed by at least one processor on the network 50. For example, each slide imager 52 includes programmable processing and data storage capabilities, and the AOI is calculated locally based on a combination of the low resolution image obtained at stage 108 and program parameters stored on the data store 54. In another example, the AOI is calculated remotely (e.g., on the local data store and application server 54), and the coordinates are transferred to a slide imager 52 configured to obtain a high resolution image. In general, the relevant AOI for a blood smear should be selected from within the area of the smear termed in the prior art as the monolayer, where individual blood cells are closely spaced but not overlapping. For example, the dimensional boundaries of the monolayer within the imaged smear is computed from the low resolution image information (e.g., from stage 108) using programmable image processing algorithms, such as spatial color frequencies and binarized texture analysis. In another example, the dimensions of the AOI are specified by a user to be rectangular (e.g., 1 mm×3 mm), where the distance scanned along the blood smear in the direction of changing smear thickness is longer than the distance scanned across the smear in the direction in which the sample thickness remains more or less constant. This allows an individual reviewer (72, 74, 76) the opportunity to choose higher or lower cell density, within the area generally termed the monolayer, according to his or her preferences.

In general, the highlighted group of process elements 114 indicates that the system can adjust the size of the AOI to ensure that a large enough image is taken for a particular patient population and a smaller image taken for another population. For example, smears from patients with abnormally low WBC counts will contain fewer WBC's per unit area of AOI than normal; accordingly, in order to image an appropriate number of cells, the AOI is increased from the default area. Image size is an important factor in determining system throughput, and it impacts other network (50) operating costs as well.

At stages 116 and 118, a high resolution image of the AOI is captured. In general, a high resolution image includes a plurality (n) of 100× magnification sub-images (e.g., image tiles) of the AOI. An AOI image file is created via an imaging system installed on the slide imager 52, and coupled to a frame grabber board. As an example, and not a limitation, the imaging system includes a Dalsa 2 megapixel CCD camera with a 1920×1080 pixel sensor that operates up to 30 frames per second and is coupled with a compatible frame grabber board (e.g., from Matrox or Dalsa). In an embodiment, the local data store and application server 54 is operably coupled to the slide imaging system 52 such that the imaging system on the slide imager 52 is connected to a frame grabber board installed in the local data store and application server 54. In this configuration, the application server 54 receives and processes both the image data and the corresponding slide position information (e.g., slide stage coordinates). The server 54 is configured to store each of the n high resolution sub-images individually, assemble the sub-images into at least one large image, and store the at least one large image.

In another embodiment, the slide imager 52 is a line scan system such as the Aperio ScanScope® System. In general, this type of slide scanner is configured to create a seamless true color digital image of an entire glass slide or an AOI on a glass slide. As described above, the AOI is calculated from the low resolution image obtained at stage 108. For example, an auxiliary camera is disposed on or within a line scan system, and is configured to send image and slide identification information to the application server 54. The application server 54 computes the AOI, and sends the appropriate coordinates to the line scan system. The line scan system obtains the high resolution image of the AOI (i.e., not an image of the entire slide), and sends the image information to the server 54.

Preferably, the slide imager 52 can process 60 areas per hour based on an imaging rate of 0.1 sqmm/sec (i.e., 14 MB/sec), and the resulting pixel resolution (i.e., the combination of the optical enlargement and the CCD pixel density) should be less than 0.2 um.

In an embodiment, the captured images (e.g., tiles, scan strips) are assembled into a single image at stage 120. At stage 122 the server 54 performs a count of the number of WBC's imaged (n WBC). The WBC count is made using an image processing software application running on the server 54. For example, WBCs are identified within the AOI using a spatial color frequency algorithm to distinguish the characteristic size, shape and characteristic stained color of WBC's. Other image and color processing algorithms are also envisioned. The location of each identified WBC is calculated. The count result n WBC is compared to a programmable parameter at stage 124. If n WBC is below a low threshold (e.g., less than 300), then the server 54 adjusts the size and location parameters associated with the AOI at stage 126. The adjustments to the image can be cumulative (i.e., add new image areas to the AOI without imaging the previously imaged areas), or duplicative (i.e., re-image the entire new AOI). For example, if the n WBC is below the programmable parameter (e.g., 300), the area (e.g., length, width) of the AOI can be increased, and the imager 52 will image the new tiles, or line scans if the imager 52 is a line scanner. A decision is made at stage 128 to proceed with scanning the adjusted AOI or to notify an operator. The image capture process 114 is completed at stage 124 when n WBC of the assembled image is determined to be greater than the low threshold (e.g. greater than 300).

At stage 132 the WBC location data created as part of the WBC count in stage 122 is stored on the local data store and application server 54 (i.e., image server). At stage 134, the high resolution AOI image is compressed to reduce the file size (e.g., JPEG2000, TIFF). At stage 136 the resulting image file, together with the snapshot data and other image metadata not separately stored, is stored in the image table 162 on the image server 54. After the image file is stored at stage 136, the process returns to stage 104 and proceeds with scanning the next slide in the batch if any, or to notify an operator 138. If scan process is incomplete at stage 140, the operator will intervene at stage 142 to address potential scan issues (e.g., rescan the low resolution image, rescan the AOI, perform a manual review). If the scan process is complete at stage 140, scan information is logged and distributed 144, a scan complete stage is indicated 146, and a load/unload sequence is initiated 148.

In general, the web server 60 includes a relational database with a plurality of correlated tables, wherein each table includes data fields consisting of various data types. As an example, and not a limitation, the web server 60 is configured to replicate and store the contents of the image table 162 and the WBC table 160, and to provide access to those tables 160 and 162 via the internet 70. The image server 54 is configured to keep the HIPAA-sensitive and private contents of the patient table 164 secured in a secure data store 56 and inaccessible from the web server 60 or any other unauthorized access.

The web server 60 is additionally configured to record and store data which applies to one or more image servers 54. For example, the web server 60 stores in a site table 170 a listing of each of a plurality of image servers 54 in the network 50, wherein each image server 54 is associated with one customer site identified by a unique index variable (i.e., Site ID). Additionally in a user table 168, a listing of reviewers (72,74,76) categorized by their affiliation, including employees of the lab in which the image server 54 is located, employees of other organizations with which that lab is affiliated, and third-party contractors to labs or to the network operator. The user table 168 also contains a state variable that is maintained by the workflow scheduling application 62 indicating the work-in-process (WIP) status of each user; the available states including, but not limited to, logout, open, and full. Additionally in a site approval table 166 a listing of site approvals for each reviewer (72,74,76) in the user table. The site approval table contains variables which are set for each user and which are used by the workflow management application 62 to constrain the distribution of an image file uploaded from any given image server site to any one network reviewer (72, 74, 76) based upon affiliation, skill, quality, speed, pricing or specialty, or other criteria chosen by a site administrator or specific to a particular reviewer. For example, for each user and indexed to each site, the site approval table lists a variable $n_{app}$, such variable set to $n_{app}$=zero if the user is not approved to review images from that site, set to $n_{app}$=1 for users that are employees of a lab at that site, and set to $n_{app}$>1 for users not employed by that site and approved to review images from that site, the specific setting of $n_{app}$>1 corresponding to one or more organizations with which network reviewers are affiliated. Additionally, in a review queue table 174 a listing indexed by Image ID of all image files stored in the image table 162 not yet reviewed. In general, the review queue 174 includes pointers, or other indices, to the AOI image files stored in the image table 162 on the web server 60. Along with each image file entry in the review queue table 174, for example, will be stored various parameters used by the workflow management application 62 for scheduling the review of each image file.

The users of the hematology network 50 maintain a plurality of workflow preferences on the web server 60. An administrator assigned to an image server 54 or group of image servers (i.e., site administrator) enters parameters into the web server 60 (i.e., site preferences) that configure the operation of the slide imagers 52, image servers 54, and web servers 60 as they relate to images originating from his particular site. These site preferences are stored on the web server 60 in a site preferences table 172.

At stage 150, the web server computes for each image file several parameters used subsequently by the workflow management application 62. As an example and not as a limitation, these calculations are made using image file metadata, including a time/date stamp set when the image file was stored on the image server 54 in stage 136, data stored in the site preferences table 172, including, but not limited to, one or more variable time delays that apply to each of one or more categories of network user (e.g., $n_{app}$ above), and calendar-based data that allows scheduling parameters to be set for individual blocks of time, or in a recurring calendar-based pattern, or in any combination. At stage 152 these computed parameters (i.e., release times $t_n$) are stored in the review queue table 174.

Figure 4:
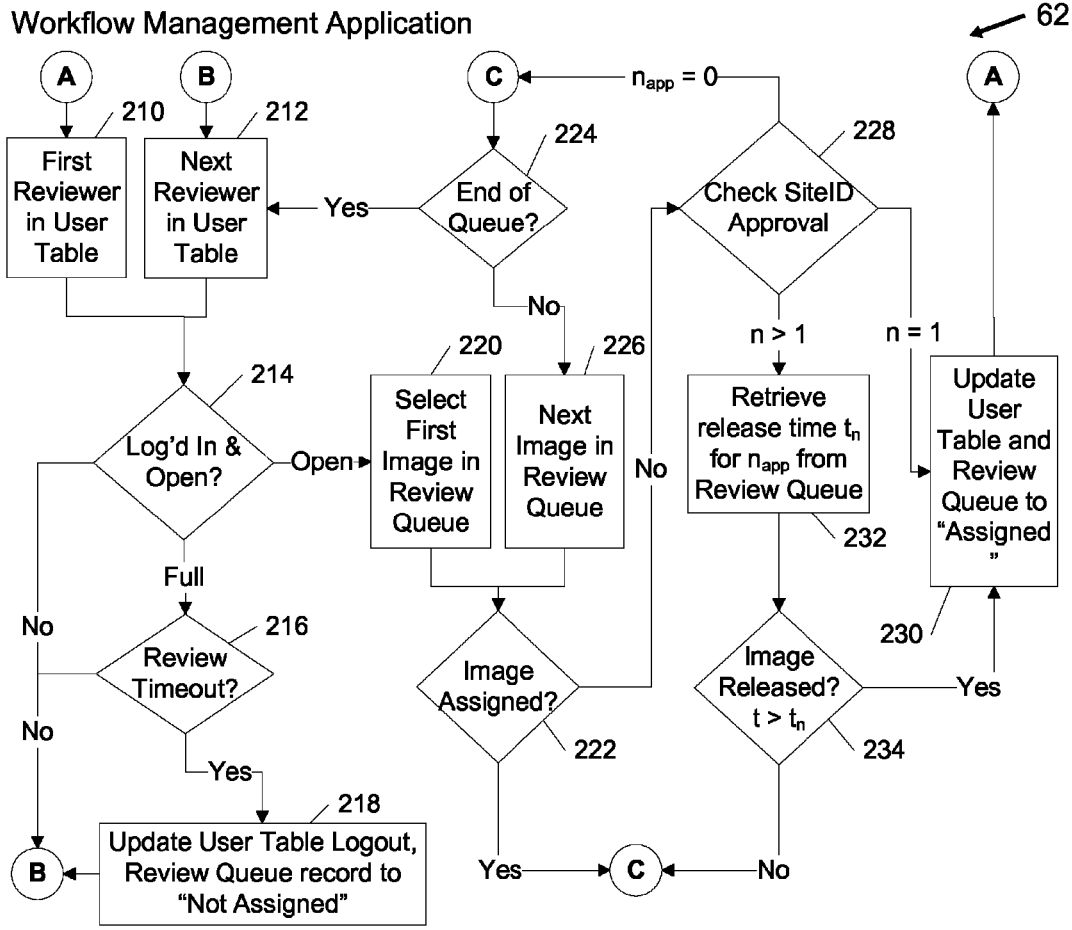
FIG. 4 is a process diagram of web server and workflow management system.

In operation, referring to FIG. 4, with further reference to FIGS. 2 and 3, a process 200 for image distribution and work scheduling for clinical hematology using the network 50 includes the stages shown. The process 200, however, is exemplary only and not limiting. The process 200 may be altered, e.g., by having stages added, removed, or rearranged.

In reviewer scheduling 200, the workflow management application 62 distributes for review the high resolution AOI image of a sample to at least one reviewer (72,74,76) over the network 50. The reviewers (72,74,76) are, depending upon their schedule, logged into individual sessions on the web server 60 from computer workstations connected to the Internet 70 via a web browser. The workflow management application 62 monitors and maintains a queue of image files for each reviewer (72,74,76) and/or groups of reviewers. Each reviewer (72,74,76) is notified that there is work for them to perform.

At stage 202 each site administrator sets Site Preferences that configure the operation of the hematology network 50 for images uploaded from image servers 54 associated with that site. These preferences are stored in the site preferences table 172 on the web server 60. As an example these site preferences may include scheduling parameters, such as review timeouts and user category time delays for image release. The site preferences may also include review parameters, such as manual diff WBC counts and RBC sample size.

As an example, and not a limitation, at stage 210 the workflow management application 62 selects the first entry in the user table 168, the user table sorted by user category, and further by user id, or by any other hierarchy selected by the network operator. At stage 214 the application checks the user table record to determine user status. If the user status is set to logout, the application proceeds the next record in the user table 168 at stage 212. If the user status is set to full, the application proceeds to stage 216 and checks the review queue table 174 to determine which image is assigned to the user, how long it has been assigned, and compares that time with the review timeout preference in the site preference table 172. If the time assigned exceeds the timeout preference, the application logs the user out, updates the user status to "logout" in the user table 168, updates the image file record in the review queue table 174 to "unassigned", and proceeds to the next user in the user table 168 at stage 212. If the time assigned does not exceed the timeout preference, the application proceeds directly to stage 212.

If at stage 214 the user status is determined to be open, the application proceeds to stage 220 and selects the first image in the review queue table 174, the review queue sorted by a hierarchy selected by the network operator or by a site administrator. For example, the review queue is sorted in ascending order by the time/date stamp in the image file metadata, where the oldest file in the review queue table 174 is listed first. At stage 222 the application checks a state variable in the review queue table 174 to determine if the image file has been assigned to a reviewer for review. If the file is assigned the application proceeds to stage 224 and determines whether it has checked the last image file listed in the review queue table 174; if it has checked the last image the application proceeds to stage 212 and selects the next reviewer in the user table 168. If it has not checked the last image in the review queue table 174 the application proceeds to stage 226 and selects the next image file in the review queue table 174.

If at any time during this cycle through the review queue table 174 the application determines at stage 222 that an image file in the review queue table 174 is unassigned, the application proceeds to stage 228 and retrieves the value of $n_{app}$ from the site approval table 166 that corresponds to both the open user selected at stage 214 and the site ID of the unassigned image file selected at stage 222 and stored in the review queue table 174. If the value of $n_{app}=0$, then the application determines that the selected open user is not approved to review the selected unassigned image file, and proceeds to stage 224. If at stage 228 the retrieved value of $n_{app}=1$, then the application determines that the open user is approved to review the selected unassigned image file, and proceeds to stage 230 where the application updates the selected user record in the user table 168 to "full" and the selected image file record in the review queue table 174 to "assigned". If at stage 228 the retrieved value of $n_{app}>1$, then the application determines that the open user is approved to review the selected unassigned image file subject to one of several time constraints set in the review queue table 174, and proceeds to stage 232. At stage 232 the application retrieves from the review queue table 174 the value of the release time variable $t_n$, such $t_n$ set at stage 152, that corresponds to the selected $n_{app}$, and proceeds to stage 234. At stage 234 the application determines whether the release time $t_n$ set in the review queue 174 for the selected site approval $n_{app}$ has been satisfied (e.g., current time t>release time $t_n$); if it has been satisfied, then the application proceeds to stage 230 as above, and if it has not been satisfied, the application returns to stage 224.

In another embodiment the workflow scheduling application is configured to assign more than one image to any reviewer at one time. In general, the maximum number of images simultaneously assigned to each reviewer functions as a WIP buffer in the queuing network. This maximum WIP for each reviewer can serve to maintain reviewer utilization (minimize idle time) in cases where the network is experiencing performance disruption. As an example, and not as a limitation, each site administrator may specify a reviewer queue size $q_r>1$ (where 1 is the system default) which configure the workflow management application 62 to continue to assign new image files to an individual, group, or class of reviewers (72, 74, 76) at stage 214 (i.e., to consider the user "open") until the total number of images assigned to that reviewer reaches the reviewer queue size $q_r$.

Figure 5:
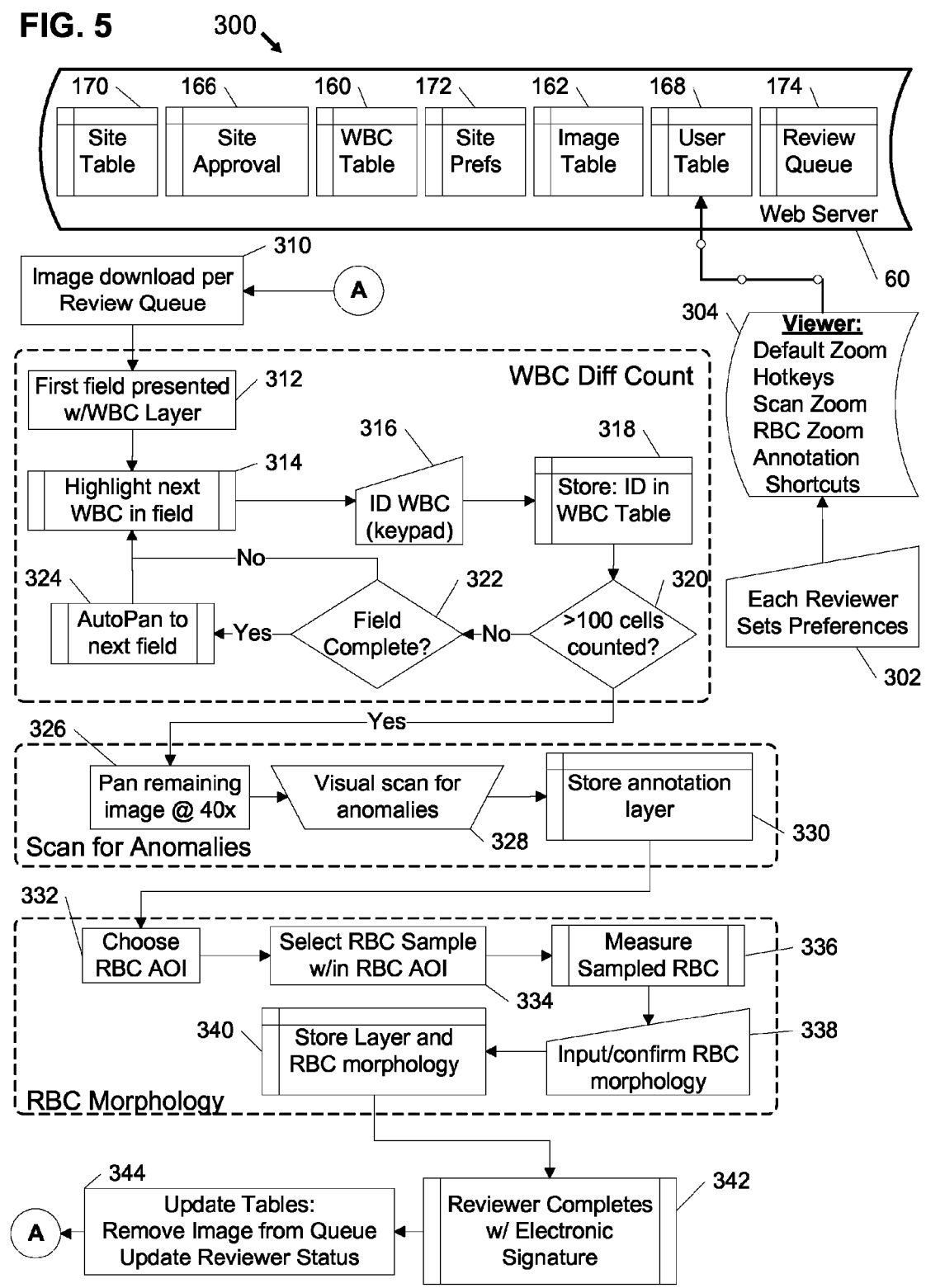
FIG. 5 is a workflow diagram of an exemplary hematology image review.

The network 50 presents the high resolution AOI image of a blood smear to a reviewer (72,74,76) on a computer workstation, facilitates the examination of the smear, including the manual WBC count, and allows the reviewer to record the results of the examination. Referring to FIG. 5, as an example and not a limitation, the reviewer (72,74,76) analyzes an image file in accordance with a review workflow 300. At stage 310, the images and metadata on the web server 60 are available for download to a reviewer (72,74,76), and a specific image file is downloaded to the workstation of a reviewer (72,74 76) based on programmable parameters in the workflow management application 62. For example, a review queue table 174 includes image information for images which are assigned to a particular reviewer by means of a parametric setting, or as a result of workflow logic.

In general, the network 50 presents the image of a blood smear to a reviewer 72,74,76 on a computer workstation through a GUI, facilitates the examination of the smear, the elements of such examination are as established in the prior art process 24, including the manual WBC count, and allows the reviewer to record the results of the examination. The reviewer uses a computer which runs a web browser and other software application which is designed for review of blood smears. Typically, these applications include a GUI and allow the reviewer to select among several magnifications (image zoom), pan one full field at a time, and includes a "Magnification Window" which presents a portion of the image at a selectable multiple of the magnification in the main window.

At stage 302, a reviewer user (72,74,76) enters and stores user preferences for image review 304 in the user table 168 on the web server 60. For example, a reviewer (72,74,76) sets the default zooms for received image files (e.g., a scan zoom, and an RBC zoom). A reviewer (72,74,76) also configures their review environment by setting, for example, keyboard hotkeys for WBC classification and annotation shortcuts.

At stage 312, the first field of the AOI image is presented to a reviewer (e.g., 72,74,76) based on the reviewer's previously stored preferences 302. For example, a reviewer sets the default zoom preference to 20× magnification for new images. In an embodiment, the image presented 312 is a combination of an image file from the image table 162 and the WBC location data stored in the file corresponding to the selected image in the WBC table 160, such combination called the "WBC location layer". In this embodiment the review application can highlight the previously detected and counted WBC's for the reviewer using the location layer data. Further, the WBC table, and correspondingly the WBC location layer, may include WBC location information entered and stored in the WBC table by a reviewer during a prior review session.

At stage 314, the application selects the image of a WBC in the WBC location layer and highlights it on the display for the reviewer (72,74,76). The reviewer can also separately identify and select images of other material in the sample, including, but not limited to, WBCs (i.e., WBCs in the image which were not previously stored in the WBC table), RBCs, nucleated RBCs, other cells, cell fragments, or anomalous material, displayed in the field. Typically, the reviewer uses a point and click feature of an image review software application to select a particular feature in the image. In general, the image review application 300 is configured to auto-zoom on the currently selected area of interest (e.g., a WBC) using the aforementioned magnification window; this allows the reviewer to observe fine detail using high magnification on one portion of the image while visually scanning the remainder of the selected field of view at a lower magnification.

At stage 316, the reviewer enters information about the highlighted item with a keypad, pointing device, or other data entry system. This information includes, but is not limited to, the classification of a selected WBC as well as size information and other comments generally termed WBC morphology, and classification and description of selected RBCs, nucleated RBCs, other cells, cell fragments, or anomalous material, as established in the prior art process 24. The information entered at stage 316 is stored in several locations on the image server 54, including the WBC table 160, at state 318.

At stage 320, the number of WBCs that have been classified by the reviewer and stored in the WBC table is verified. For example, based on sampling logic widely accepted in the prior art process 24, a reviewer (72,74,76) is expected to count at least 100 WBC in the AOI of a blood smear sample.

If the total number of WBC's classified by the reviewer is less than 100, the application proceeds to stage 322. If a reviewer confirms that all of the relevant material, including but not limited to WBCs, NRBCs, and anomalous cells and material, in a particular field of view have been identified at stage 322, the review application will automatically pan to another image field at stage 324. The application then returns to stage 314 where the next WBC in the field is highlighted.

Selecting a WBC and panning through the image can occur with various levels of automation. For example, in an "assisted mode review", the review application 300 utilizes a reviewer's preferences 304 with image metadata (e.g., WBC location information in the WBC table 160) to automatically select a portion of the image file that contains some number of WBCs. Additionally, the present invention can overlay the WBC location layer information onto a portion of the image file at a magnification chosen as a user preference 204 (e.g., 20×, 30×, 40×, 50×). For example, starting in the upper left hand corner of the AOI image and progressing across the file in a raster pattern, each WBC identified in the WBC location layer is highlighted in succession and a portion of the AOI image file centered on the location of each WBC will be presented in a magnification window. A reviewer will classify (e.g., "click off") each cell as it is presented using his preferred keyboard hotkeys or other input device. The classification of each WBC classified is appended to the WBC table 160. The review application 300 will automatically advance to the next WBC in the selected portion each time a classifying entry is made. In this way a manual differential WBC count will be made until the total number of cells counted and classified reaches the required threshold value. In an embodiment, an image processing algorithm (e.g., pixel counting) included in the review software 300 will support the reviewer in automatically or semi-automatically measuring the dimensions of the highlighted features (e.g., cells, fragments, material) being reviewed.

Once the total number of WBC's classified by the reviewer at stage 320 reaches the required threshold value set in the site preferences table 172, such value set at 100 cells as a default, the reviewer will change the magnification (e.g., 20×, 40×, 60×, 80×, 100×) at stage 326, and visually scan the AOI image for other anomalies at stage 328. For example, a possible anomaly or abnormality that may be present in any sample of human blood may also have a low occurrence rate (i.e., also termed "rare events"). One example of such a rare event would be the presence of the malaria parasite. As described in the prior art, in order to determine that the abnormality is not present in a sample, an established number of high-power fields must be examined; this area can exceed that required for a manual diff or other routine inspection. In one example, such minimum inspection area may be set as a site preference in the site preferences table 172; in another example, such minimum inspection area may be called out as a separate inspection requirement for an individual image file. In an embodiment, image processing algorithms are accessed by the review application. These algorithms are configured to process any portion of one image file, or any subset of image files, for "rare event" defects and flag the defects for review in a manner similar to the identification and counting of WBC's in stage 122. The image processing algorithms can be installed on web server 60 and downloaded to the reviewer as required. At stage 328, the reviewer enters comments or otherwise adds annotations to the image which is then stored at stage 330 as an image annotation layer appended to the image file in the image table 162.

In general, the reviewer can examine the AOI image of a blood smear sample for other hematological data. For example, at stage 332 the reviewer (72,74,76) chooses an area of interest within the blood smear image to display, examine and measure the size of red blood cells (e.g., RBC AOI), an operation termed "RBC morphology" in the prior art process 24. At stage 334 a plurality of RBC's within the RBC AOI, the number of which is set as a site preference in the site preference table 172, is selected either manually by the reviewer using the pointing device, or automatically by the review application using a spatial color frequency algorithm in a fashion analogous to the method of selecting WBC in stage 122. At stage 336, the diameter measurement of one or more selected RBCs is acquired manually by the reviewer as established in the prior art 24, or manually by the reviewer using feature measurement tools included in the review software that use an image processing algorithm (e.g., pixel counting to estimate dimensions), or automatically by the application using pixel counting algorithms applied to the RBC's selected at stage 334. The reviewer confirms the average measurement and inputs RBC morphology data as comments at stage 338. The RBC data is stored on the web server 60 at stage 340. For example, the RBC data and comments are stored on the web server and in the image table 162 as an annotation layer appended to the image file.

At stage 342, the reviewer completes the review of the AOI image. For example, the reviewer enters a digital signature as verification that the review is complete. The application then updates the scheduling parameters stored on the web server for the completed image file. For example, at stage 344 the image file status field in the review queue table 174 is updated to "complete" and the user table 168 is updated to "open."

In an embodiment, the web server 60 is configured with a billing code segment which enables the collection of information on the number of blood smear images reviewed by the user (72, 74, 76), and a computation of costs associated with the user. Contracted billing rates, expressed on a per review or per time unit basis, are recorded for specific users and sites on the web server 60. Such information is collected and computed by the operators of the network 50. The report generator 58 is configured to report services rendered by user to each site administrator on a periodic basis. In another embodiment, the users (72,74,76) indicate (e.g., post) offered prices for review services onto the web server 60. If a lab has specified a preference that the review of any image or group of images are to be bid out at auction, the workflow management application 62 will match the image to lowest price bid by any approved reviewer, place the image in the reviewer queue.

In an embodiment, the workflow management application 62 is configured to select a subset of all reviewed image files for further quality assurance (QA) review. For example, site administrators maintain QA preferences in the site preferences table 172 that are used by the workflow management application 62 to determine how that sample is taken and how the QA review is performed (e.g., sampling frequency, sampling method, QA review method). The site approvals table 166 includes a listing of which users (72,74,76) are approved to perform QA review on images from each different site. As an example and not a limitation, the workflow management application 62 releases images to available QA reviewers in a manner similar to that specified in FIG. 4, and the individual QA reviewers examine, report on, and annotate sampled images in a manner similar to that specified in FIG. 5.

Additionally, the review application 300 is configured, according to site administrator preferences, to present to a QA reviewer the data taken during prior reviews of the image file, or, conversely, to withhold that prior review data from a QA reviewer. In an embodiment, while performing a QA review, the review application is configured to access the WBC location data saved after a prior review in the WBC table 160 on the web server 60 and display such data for the QA reviewer. As an example, the data includes the WBCs identified by the image server at stage 122 and classified by a prior reviewer at stage 316, and WBCs identified by a prior reviewer at stage 314 and classified by a prior reviewer at stage 316. In this manner, the review application allows the QA reviewer to classify each of the cells previously classified by a prior reviewer in a manner similar to that described in FIG. 5, and then appends this QA review classification data to the corresponding WBC record in the WBC table 160.

In general, the network 50 is configured to monitor the accuracy of reviewers (72,74,76) in classifying blood cells during reviews performed on the network 50. The web server 60 includes a QA software application which is configured to query the information stored on the web server to calculate statistical measures of reviewer accuracy. The QA application queries the Image Table 162 and the WBC table 160 for each user in the user table 168. For each user (72,74,76) the query returns a list of all the WBCs classified by that user and by a QA reviewer, as well as for each WBC in that list the following; a pointer to the relevant image files, QA reviewers' user IDs, and the WBC classification by both the user and the QA reviewer. From this set of classified WBCs, the QA application computes how many times the user classification agrees with subsequent QA classification, such number expressed as a percentage of the total WBCs in the list. This percentage is stored in the user table 168 as a QA rating.

Similarly, in an embodiment with reference made to FIG. 7, the web server 60 is configured with an image processing software application that classifies cells within the high magnification image file. The output of this classification application is correlated with the review information input by a reviewer to establish a QA rating for both the reviewer and the software.

In general, the network 50 is configured to report to site administrators data used to evaluate the quality of the work performed on the network by the users (72, 74, 76). In one embodiment the report generator 58 is configured to generate reports for each site administrator. As an example and not a limitation, those reports compare the results of the review and QA review of each QA sampled image and lists each discrepancy. A QA summary report aggregates the above data across a large number of QA reviewed image files sampled for that site. A reviewer performance report includes the QA rating for each reviewer approved for that site.

In an embodiment, the operation of the network 50 generates a database of high magnification images of blood smears and related metadata collected from multiple patient populations, such images and metadata which have been created, qualified, and annotated by approved reviewers (72, 74, 76) and further qualified by QA reviewers. The operation of the network 50, therefore, creates an aggregated, qualified, hematology image dataset. The dataset, and any subset of that dataset (e.g., data sorted by site or by patient type), serves as reference image dataset for automated image retrieval and classification software applications deployed on the network 50 to be used by reviewers (72, 74, 76), by QA reviewers, and by the operators of the network. Such image retrieval and classification software applications perform, but are not limited to, the following image processing functions; image extraction, feature extraction, class screening, image retrieval, and cell classification.

In operation and referring to FIGS. 7A and 7B, with further reference to FIGS. 2, 3, and 5, the web server 60 stores image files uploaded from at least one image server 54, indexed in the image table 162, and with WBC location and related metadata stored in the WBC table 160. As an example and not a limitation, the hematology network 50 is configured to automatically retrieve images of WBCs from high magnification images of blood smears and classify those WBCs at stage 500.

The web server 60 is configured to run an image processing software application that extracts images of individual blood cells from image files stored in the image table 162 using location data of each blood cell stored in the WBC table 160. In an embodiment, this image extraction application is used to create a library of classified cell images; such reference image extraction application is shown at stage 501. At stage 502 the application selects from the image table an image file and at stage 504 decides whether or not the file has been both reviewed and QA reviewed. If not the application returns to stage 502 and selects the next image file. If the file has been both reviewed and QA reviewed, at stage 506 the image extraction application selects the first WBC listed in the WBC table 160 corresponding to the selected image file. If the cell class input by the reviewer (i.e., ClassR) and a QA reviewer (i.e., ClassQA), such information stored in the WBC table 162, are the same at stage 508, the extraction application proceeds to crop extraneous image data from around each subject cell at stage 510. The resulting cropped image of an individual, classified WBC is then stored at stage 512, together with its related image metadata including, but not limited to, cell class, in a reference cell library table 176 stored on the web server 60. The application then proceeds to check the remaining WBC images in the file, checking if any remain at stage 514. Typically each reviewer (72, 74, 76) classifies, depending upon site preferences, a minimum of 100 WBCs during a manual differential blood count, and each image previously selected by the workflow scheduling application 62 for QA review has had each of those cells classified by a QA reviewer; the extraction application therefore extracts from each selected image file some number of the 100 cropped images of cells, such number equal to the number of cells for which two approved reviewers have recorded the same classification. At stage 515 the application returns to stage 502 to select the next image file in the image table 162; if all files in the table have been processed the image extraction process is complete at stage 516.

The web server 60 is further configured to compute for each cropped image of an individual cell stored in the cell library table 176 a plurality of values that describe the image of the cell (e.g., image features); such feature extraction application is shown at stage 518. At stage 520 a WBC image is selected from the cell library table 176. At stage 522 the feature extraction application computes the value of each of a set of N features (i.e., WBC feature set); such feature set includes, but is not limited to, cell texture, cell color R, cell color G, cell color B, cell area, edge transition, edge distribution, outlining polygon. At stage 523 the N feature values are stored with the cropped image in the image library table 176. At stage 524 the application returns to stage 520 to select the next WBC image in the cell library table 176; once all WBC cell images in the cell library are processed, feature extraction is complete.

In general, images of stained cells from a peripheral blood smear slide are identified and classified as described in the prior art process 24. As an example cited in the prior art, the cytoplasm of eosinophilic leukocytes contains granules which stain a bright and distinct orange-red color; it is the color of these granules that primarily defines this cell classification. As an example, and not as a limitation, the color feature "cell color R", a red component color intensity measurement computed at stage 520 from the image of any cell classified as an eosinophil is very likely a higher value, whether relative to other color measurements or as an absolute value, than that same color feature computed from the image of a WBC with a different classification.

The network 50 is further configured to identify statistical outliers within the plurality of cell images of each cell class stored in the cell library table 176 (i.e., screen the class) on the web server 60. In general such class screening is performed using both computational methods and by manual inspection of image feature datasets and cell images by network users (72, 74, 76). As an example, and not as a limitation, class screening of WBCs is shown at stage 526. At stage 528 a user selects a cell class for screening. At stage 530 a class screening software application queries the cell library table 176 for the selected cell class and at stage 532 selects the first n of total N image features for screening. The screening application then computes at stage 534 descriptive statistics on each value stored in the cell library table 176 within the selected class for the image feature n. As an example and not a limitation the descriptive statistics include image feature n sample mean and image feature n sample standard deviation. At stage 536, the application identifies as a potential outlier any cell image within the selected class with an image feature n value that deviates from the image feature n sample mean for the selected class by more than 2 times the image feature n sample standard deviation. If there are no potential outliers in the plurality of cell images in the selected class with feature n, the application proceeds to stage 544. If one or more potential outliers are identified, at stage 538 the application displays on the user workstation the image of one such cell identified as a potential outlier together with a graphical representation of the distribution of all the values of feature n for the selected class (e.g., a sample frequency plot). At stage 540 the user screens the image and chooses to include or exclude the image from the reference dataset. At stage 542 the library table 176 is updated; a state variable in each cell image record is set to include or exclude each image as a reference image based upon the screening results above. At stage 544 the application returns to stage 536 to screen the next potential outlier. If at stage 544 each potential outlier has been screened the application proceeds to stage 546 and returns to stage 532 to screen the next image feature (i.e., feature n+1). If at stage 546 each of the N features has been screened, the application proceeds to stage 548 and returns to stage 528 to screen the next cell class. After each cell class has been screened, the process of class screening is completed at stage 550.

Once a reference dataset has been established it can generally be used to make comparison-based classification of new cell blood cell images. For example, automated image retrieval and cell classification of subject WBC images is shown at stage 560.

At stage 562, a new blood smear image is uploaded from an image server 54 with high magnification images stored in the image table 162 and with WBC location information stored in the WBC table 160. At stage 564 the image extraction application is run as outlined from stages 506 to 514. At stage 566 the cell images are excluded from the reference dataset. At stage 568 the feature extraction application is run on the above new WBC images as outlined from stages 520 to 524.

The web server 60 is further configured with a software application that compares image feature values extracted from a subject image of a cell to similar image features in a reference set of classified cell images in order to choose one or more images from the reference set that most closely match the unclassified cell image; such automated image retrieval application is shown at stage 570. As an example and not as a limitation, at stage 572 the image retrieval application selects the first cell image from the reference set stored in the cell image library table 176. At stage 574 the application compares each image feature n of the reference image to each image feature n of the subject new WBC image. The comparison application computes the difference between the subject value and the corresponding reference value of each feature n, expresses that difference as a percentage of the subject value, and then computes a comparison of the subject cell and the reference cell across all the N features by summing the absolute values of each of those N feature percentage differences, such sum termed the match deviation. At stage 576 the application returns to stage 572 and selects the next reference cell in the library. Once the subject cell image has been compared to each image in the reference dataset, one or more reference images are selected (i.e., retrieved) at stage 578, such number of images set as a site preference in the site preferences table 172, and such that the images selected are those with the smallest match deviation values to the subject cell. The library table index values of the selected best matched cells are stored in the WBC table 160 record for the subject cell.

The web server 60 is further configured with a software application that displays to a reviewer (72, 74, 76) on the reviewer workstation the retrieved best match reference images together with the stored classification of each of those reference images; such classification application is run at stage 580. The reviewer (72, 74, 76) confirms the classification of the subject cell at stage 582. In an embodiment, this application is provided to a reviewer (72, 74, 76) during a manual review and may be selected by a reviewer at stage 314 to provide reference images to assist a manual classification.

In general, once a reference dataset has been established, the feature extraction, retrieval and classification applications are run on every WBC listed in the WBC table 160 and in an image file stored in the image table 162, in advance of image review at stage 300 by a reviewer (72, 74, 76). For example, the classification application compares the classifications of the 10 best matched reference images saved in the WBC table 160. If all ten classifications are the same, the application will display, at stage 314, a message, on the workstation of the reviewer (72, 74, 76), that the subject cell is of the same class as the reference cells, and such automated classification is stored on the web server 60 in the WBC table 160.

In operation, referring to FIG. 6, with further reference to FIG. 2, a process 400 for obtaining a high resolution image of an AOI on a blood sample slide using the network 50 includes the stages shown. The process 400, however, is exemplary only and not limiting. The process 400 may be altered, e.g., by having stages added, removed, or rearranged.

At stage 402 a blood smear slide sample is received. In general, the slide sample is prepared with an automatic slide preparation tool, but a blood smear sample may also be prepared manually. The slides generally include a 25 mm×25 mm area of blood which has been stained. A blood smear sample slide generally includes identification information such as a patient's social security number, lab number, and lot number. Slide samples can be received individually or in batches. A slide image or 52 can be equipped with an automatic loading mechanism configured to transport slides from a loading area to an inspection area. The loading mechanism may also include a slide identification device, such as a barcode reader, and the imager 52 is configured to recognize and store the identification information.

At stage 404, a low resolution image of a blood smear slide is obtained. In general, the low resolution image includes a substantial portion of the blood smear sample as well as the identification information. The imager 52 may include a low resolution CCD camera configured it to obtain the low resolution image prior to placing the slide in the high magnification optical path. In general, the low resolution CCD camera is coupled to an image capture device such as a frame grabber board. The low resolution image is stored on the local data store and application server 54. In that the low resolution image contains patient information (e.g., the patient's social security number), it will persist within a secure data storage unit 56 if at all.

At stage 406, the application server 54 includes at least one computer program embodied in a computer readable medium for enabling image processing, and is configured to analyze the low resolution image. For example, a blood smear slide includes a barcode, or text based identification information, and the application server 54 is configured to recognize and store the identification information. The application server 54 is also configured to assign a handling serial number to the low resolution image.

At stage 408, the application server 54 includes at least one computer program embodied in a computer readable medium for enabling analysis of the low resolution image. The application server 54 is configured to calculate an area of interest (AOI) based on the visual properties of the low resolution image. For example, the AOI is selected using an appropriate image processing algorithm, such as spatial color frequencies, binarized texture analysis, or similar. The AOI is generally located in a portion of the blood smear where there are no overlapping cells (i.e., monolayer). The AOI need not be one continuous region, as the image analysis may identify several disconnected regions (i.e., islands, pockets) of interest. In general, the AOI will include a plurality of high-resolution images (i.e., N number of images or scans).

Stage 409 includes an iterative process for determining and adjusting the AOI based on the white blood cell count (WBC) within the AOI. At stage 410, at least a portion of the AOI on the blood smear slide is positioned under a high-resolution optical path. Typically, the high-resolution image (e.g., 60×, 80×, 100×) is obtained through oil immersion objective lens and a high resolution CCD camera coupled to a frame grabber board. In an example, the frame grabber board is located within the image server 54. In a networked environment, however, a single application server 54 including a frame grabber board can be configured to receive image is from a plurality of imaging systems 52. Also, the imaging system 52 can be a line scanner configured to scan the AOI.

At stage 416, the application server 54 includes at least one computer program embodied in a computer readable medium for enabling the quality, spatial and color analysis of the high resolution image. As and example, and not a limitation, the server 54 utilizes a spatial color frequency algorithm to distinguish the characteristic size, shape and the characteristic stained color of the WBCs to perform a count of the number of WBCs imaged (n WBC). Other image parameters may also be used to automatically detect other characteristics of the blood cells. At stage 418 the total count is compared to a previously stored variable, or range of variables (e.g., a required count range 'x'), to determine if a sufficient number of WBCs are in the AOI. The comparison can be based on a ratio of the area imaged (i.e., scanned) versus the required count. For example, the relationship between the number of white blood cells in an area of interest is linear, such that if half the area of interest is imaged, than half of the number of white blood cells should be counted. The server 54 is configured to determine if the count of WBCs is above, or below, the required ratio throughout the imaging process.

At stage 420, the size of the AOI can be adjusted based on the number of WBCs counted in relation to the area imaged or scanned. For example, if the number of WBCs counted is below an expected value, then the size of the AOI is increased. The increase typically includes obtaining additional high-resolution images along the horizontal axis of the original AOI, however, additions to the AOI may also include collections of new images which are not connected to the original AOI. Further, a particular portion of the AOI image may have low image quality parameters (e.g., poor contrast, low gain, low color resolution) and thus will be removed from the AOI. At stage 422 a decision is made whether a scanning retry is authorized to recapture the recalculated AOI, and the process returns to high resolution scanning operation at stage 410.

Once the required WBC count in the imaged sample is reached at stage 418, the high resolution image of the AOI is compressed and stored at stage 424. For example, a collection of images are constructed into a single AOI image and stored as a single JPEG file. The AOI image may also be stored as a collection of smaller images. In an example, each of the images is stored as a JPEG file along with position data corresponding to its location on the blood smear slide.

At stage 426, the server 54 is configured to scrub the image file, or files, to remove HIPAA sensitive data. In an example, the images are searched for areas which may include bar code markings or text or other identification of an individual patient, and the server 54 is configured to remove or mask those areas. In general, a patient's personal data will persist in a secured database 56 and the AOI image will be stored in a separate database table such that it can be linked to the patient's personal data through an indexing scheme. The indexing scheme can be encrypted or secured as known in the art.

At stage 428, the AOI image and associated metadata is uploaded to a Web server 60. In general, the Web server 60 is connected to the Internet and is configured to allow a access to the AOI image by Internet users. The internet users, however, will generally not have access to the HIPAA sensitive data associated with the AOI image.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

We claim:

1. A hematology review network comprising:
a slide imager including a low magnification optical path and a high magnification optical path, and configured to receive a blood smear slide, obtain a low magnification image of at least a portion of the blood smear slide, and obtain at least one high magnification image of a portion of the blood smear slide;
an image server operably coupled to the slide imager and configured to compute an area of interest within the low magnification image, direct the slide imager to obtain one or more high magnification images of the entire area of interest, identify a plurality of white blood cells in the one or more high magnification images, and recompute and rescan a larger area of interest in at least one high magnification image if the count of white blood cells identified in the at least one high magnification image is below a threshold value;
a web server including a workflow management application, the web server configured to store and disseminate the at least one high magnification image to one of a plurality of reviewers, the specific reviewer selected by the workflow management application based on a plurality of programmable parameters; and
at least one review station configured to communicate with the web server, display the at least one high magnification image, and receive an image information input from the specific reviewer, wherein the image information input is stored on the web server.

2. The hematology review network of claim 1 wherein the high magnification optical path of the slide imager includes a 100x oil immersion objective lens.

3. The hematology review network of claim 1 wherein the high magnification optical path includes a selectable objective head assembly.

4. The hematology review network of claim 1 wherein the slide imager is a line scan system.

5. The hematology review network of claim 1 wherein the web server includes a knowledge management application configured to provide information relating to blood smear images to the plurality of reviewers.

6. The hematology review network of claim 1 wherein the web server includes at least one social networking application configured to allow the plurality of reviewers to interact.

7. The hematology review network of claim 1 wherein the review station is configured to sequentially highlight in the displayed high magnification image the plurality of identified white blood cells (WBCs), wherein the review station displays a feature at higher magnification for detailed examination.

8. The hematology review network of 7 wherein the review station is further configured to record the position of and highlight in the display a feature within the high magnification image previously identified by the reviewer, wherein the review station displays the feature at higher magnification for detailed examination.

9. The hematology review network of claim 1 wherein the workflow management application is configured to select at least one stored high magnification image and the associated image information input by a first reviewer, wherein the image information is verified by a second reviewer.

10. The hematology review network of claim 1 wherein the image information input from the specific reviewer is a cell classification.

11. The hematology review network of claim 10 further comprising an image processing software application configured to output an automated cell classification, wherein the cell classification input from a specific reviewer is compared to the cell classification output from the image processing software application.

12. The hematology review network of claim 1 wherein the web server and image server are configured to aggregate high magnification images of blood smears and related metadata across multiple patient populations, and provide the aggregated image and metadata to a data mining application such that Health Insurance Portability and Accountability Act of 1996 (HIPAA) sensitive information is not disclosed.

13. A method for obtaining and storing a high magnification image of a blood smear sample, the method including:
storing a low magnification image of the blood smear sample;
determining an area of interest within the blood smear sample based on image analysis of the low magnification image;
obtaining at least one high magnification image of at least a portion of the area of interest;
counting a number of white blood cell in the at least one high magnification image;
adjusting the area of interest within the blood smear sample if the number of white blood cells counted is below a first threshold;

creating an image file which includes the at least one high magnification image and excludes Health Insurance Portability and Accountability Act of 1996 (HIPAA) sensitive data; and uploading the high magnification image of the area of interest to a web server.

14. The method of claim 13 further comprising:

receiving a blood smear slide including the blood smear sample and a sample identification information;

recognizing the sample identification information; and storing the sample identification information.

15. The method of 14 further comprising linking the sample identification information with the image file with an index, wherein the sample identification information and the image file persist in different storage locations.

16. The method of 13 wherein the area of interest within the blood smear sample is adjusted if the number of white blood cells imaged is above a second threshold value.

17. The method of 13 wherein creating an image file includes assembling a plurality of high magnification images to create an assembled high magnification image of the area of interest.

* * * * *